(12) United States Patent
Shantha et al.

(10) Patent No.: US 7,883,487 B2
(45) Date of Patent: Feb. 8, 2011

(54) TRANSDERMAL LOCAL ANESTHETIC PATCH WITH INJECTION PORT

(76) Inventors: Totada R. Shantha, 115 Bayberry Hills, McDonough, GA (US) 30253; Jessica Shantha, 115 Bayberry Hills, McDonough, GA (US) 30253; Erica Shantha, 115 Bayberry Hills, McDonough, GA (US) 30253; Lauren Shantha, 115 Bayberry Hills, McDonough, GA (US) 30253

( * ) Notice: Subject to any disclaimer, the term of this patent is extended or adjusted under 35 U.S.C. 154(b) by 0 days.

(21) Appl. No.: 12/338,381

(22) Filed: Dec. 18, 2008

(65) Prior Publication Data

US 2009/0311311 A1    Dec. 17, 2009

(51) Int. Cl.
*A61B 17/20* (2006.01)
(52) U.S. Cl. .............................. 604/22; 604/19; 604/112
(58) Field of Classification Search .............. 604/22, 604/20, 65, 66, 67, 116, 19, 112, 289; 424/449; 514/447
See application file for complete search history.

(56) References Cited

U.S. PATENT DOCUMENTS

| | | | |
|---|---|---|---|
| 588,479 A | 8/1877 | Roedel | |
| 385,556 A | 7/1888 | Hoke | |
| 486,902 A | 11/1892 | Shults | |
| 1,001,949 A | 8/1911 | Hanna | |
| 1,267,162 A | 5/1918 | Anderson | |
| 2,493,155 A | 1/1950 | McMillan | |
| 2,714,715 A | 8/1955 | Manier | |
| 3,163,166 A | 12/1964 | Brant et al. | |
| 3,289,671 A | 12/1966 | Troutman et al. | |
| 3,472,931 A | 10/1969 | Stoughton | |
| 3,527,864 A | 9/1970 | MacMillan et al. | |
| 3,547,107 A | 12/1970 | Chapman et al. | |
| 3,598,122 A | 8/1971 | Zaffaroni | |
| 3,598,123 A | 8/1971 | Zaffaroni | |
| 3,677,268 A | 7/1972 | Reeves | |
| 3,896,238 A | 7/1975 | Smith | |
| 3,903,256 A | 9/1975 | MacMillan et al. | |
| 3,952,099 A | 4/1976 | Smith | |
| 4,038,721 A | 8/1977 | Kendzior | |
| 4,046,886 A | 9/1977 | Smith | |
| 4,130,643 A | 12/1978 | Smith | |
| 4,130,667 A | 12/1978 | Smith | |
| 4,141,359 A | 2/1979 | Jacobsen et al. | |
| 4,164,226 A | 8/1979 | Tapper | |
| 4,166,457 A | 9/1979 | Jacobsen et al. | |
| 4,228,796 A * | 10/1980 | Gardiner .................... 604/116 |
| 4,239,046 A | 12/1980 | Ong | |

(Continued)

FOREIGN PATENT DOCUMENTS

DE    3225748    4/1983

(Continued)

*Primary Examiner*—Nicholas D Lucchesi
*Assistant Examiner*—Broke M Matney
(74) *Attorney, Agent, or Firm*—Gardner Groff Greenwald & Villanueva, PC (57) ABSTRACT

Described herein are transdermal delivery devices composed of at least one re-sealable injection port and at least one local anesthetic reservoir. The device effectively delivers anesthetic to the skin of the subject prior to puncturing the skin by syringes, needle sticks, or other instruments intended to be inserted into the skin. In addition, this device can be used to deliver various therapeutic agents for either locally or systemically.

23 Claims, 4 Drawing Sheets

U.S. PATENT DOCUMENTS

| | | | |
|---|---|---|---|
| 4,239,052 A | 12/1980 | McClaflin | |
| 4,243,052 A | 1/1981 | Bailey | |
| 4,273,135 A | 6/1981 | Larimore et al. | |
| 4,286,592 A | 9/1981 | Chandrasekaran | |
| 4,290,878 A | 9/1981 | Blanton, Jr. | |
| 4,299,826 A | 11/1981 | Luedders | |
| 4,314,554 A | 2/1982 | Greatbatch | |
| 4,314,557 A | 2/1982 | Chandrasekaran | |
| 4,325,367 A | 4/1982 | Tapper | |
| 4,335,115 A | 6/1982 | Thompson et al. | |
| 4,343,798 A | 8/1982 | Fawzi | |
| 4,362,645 A | 12/1982 | Hof et al. | |
| 4,367,745 A | 1/1983 | Welage | |
| 4,379,454 A | 4/1983 | Campbell et al. | |
| 4,405,616 A | 9/1983 | Rajadhyaksha | |
| 4,406,658 A | 9/1983 | Lattin et al. | |
| 4,419,091 A | 12/1983 | Behl et al. | |
| 4,460,368 A * | 7/1984 | Allison et al. | 424/449 |
| 4,474,570 A | 10/1984 | Ariura et al. | |
| 4,529,601 A | 7/1985 | Broberg et al. | |
| 4,539,200 A | 9/1985 | Quarfoot | |
| 4,562,060 A | 12/1985 | Broberg et al. | |
| 4,568,343 A | 2/1986 | Leeper et al. | |
| 4,746,515 A | 5/1988 | Cheng et al. | |
| 4,751,087 A | 6/1988 | Wick | |
| 4,878,892 A | 11/1989 | Sibalis et al. | |
| 4,937,078 A | 6/1990 | Mezei et al. | |
| 5,047,249 A | 9/1991 | Rothman et al. | |
| 5,135,479 A | 8/1992 | Sibalis et al. | |
| 5,378,730 A | 1/1995 | Lee et al. | |
| 5,415,866 A | 5/1995 | Zook | |
| 5,613,945 A * | 3/1997 | Cai et al. | 604/288.02 |
| 5,622,993 A | 4/1997 | McGinity et al. | |
| 5,707,641 A | 1/1998 | Gertner et al. | |
| 5,716,635 A | 2/1998 | Cody | |
| 5,858,398 A | 1/1999 | Cho | |
| 5,965,154 A | 10/1999 | Haralambopoulos | |
| 5,968,536 A | 10/1999 | Godfrey | |
| 5,993,836 A | 11/1999 | Castillo | |
| 6,017,900 A | 1/2000 | Falk et al. | |
| 6,274,166 B1 | 8/2001 | Sintov et al. | |
| 6,630,449 B2 | 10/2003 | Wastchak et al. | |
| 6,667,052 B2 | 12/2003 | Sintov et al. | |
| 6,908,448 B2 | 6/2005 | Redding, Jr. | |
| 7,470,266 B2 * | 12/2008 | Massengale et al. | 604/890.1 |
| 2002/0161018 A1 | 10/2002 | Smith et al. | |
| 2004/0208914 A1 | 10/2004 | Richlin et al. | |
| 2005/0209319 A1 | 9/2005 | Cundy | |
| 2006/0029654 A1 | 2/2006 | Cassel | |
| 2006/0134188 A1 | 6/2006 | Podhaisky et al. | |
| 2006/0223788 A1 | 10/2006 | Cathcart | |
| 2007/0014839 A1 | 1/2007 | Bracht | |
| 2007/0196323 A1 | 8/2007 | Zhang et al. | |
| 2007/0248656 A1 | 10/2007 | Galer | |
| 2007/0269393 A1 | 11/2007 | Wepfer | |
| 2007/0280972 A1 | 12/2007 | Zhang et al. | |
| 2008/0033052 A1 | 2/2008 | Wright et al. | |

FOREIGN PATENT DOCUMENTS

| | | |
|---|---|---|
| EP | 0058920 | 2/1982 |
| EP | 0060452 | 4/1983 |
| GB | 2104388 | 3/1983 |

* cited by examiner

TRANSDERMAL LOCAL ANESTHETIC PATCH WITH INJECTION PORT

CROSS-REFERENCE TO RELATED APPLICATION

This application claims priority to U.S. provisional application No. 61/132,134, filed Jun. 16, 2008, the contents of the entirety of which is incorporated by this reference.

BACKGROUND

An overarching fear of needles and needle sticks exists throughout the world. This fear knows no bounds of age, sex, or race. For many, this phobia makes visits to the doctor and dentist intolerable and often times a last resort. This ultimately results in missed doctor's and dentist's visits and inadequate healthcare treatment of various illnesses, diseases and for routine vaccinations.

For people with this phobia coupled with chronic diseases such as, for example, insulin dependent diabetes, treatment is a daunting task. These patients face the daily task of sticking their finger with a lancet to draw blood to test blood sugar. For a noncompliant patient, this complicates diagnosis and treatment of the condition, and even for the most compliant patient, the task of repeatedly sticking their finger with a lancet is extremely painful. In addition, for a compliant patient each day the patient must administer medication or insulin via an injection. After administering their medication, proper sterile techniques require one to sterilize the injection site and place a bandage where the injection took place. This process is tedious and mundane. Many people fail to follow proper sterile techniques, and as a result, the injection site may become infected. For those people who do follow this protocol, the skin is often damaged due to the constant application and removal of bandage adhesives. Thus, it would be desirable for the subject to have a patch containing a local anesthetic to numb the injection site, an antiseptic or antimicrobial agent to prevent injection site infection, and either a single use or multi-use injection port to allow for a pain free injection for as many days as needed.

SUMMARY

Described herein are transdermal delivery devices composed of at least one re-sealable injection port and at least one local anesthetic reservoir. The device effectively delivers anesthetic to the skin of the subject prior to puncturing the skin by syringes, needle sticks, or other instruments intended to be inserted into the skin. In addition, the transdermal delivery device may include a single use patch that does not include a local anesthetic refill port. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Before the present compounds, compositions, and/or methods are disclosed and described, it is to be understood that the aspects described below are not limited to specific compositions, compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a local anesthetic" includes mixtures of two or more such anesthetics, and the like.

"Optional" or "optionally" means that the subsequently described event or circumstance can or cannot occur, and that the description includes instances where the event or circumstance occurs and instances where it does not. For example, the phrase "optionally a skin permeability enhancer" means that the therapeutic agent may or may not be included.

Effective therapeutic amount refers to the amount of a compound of the present invention that offers therapeutic activity after administration to humans or animals without adverse effects. The therapeutic amount of local anesthetic compounds is referred to as concentration of the active compound and the volume administered.

Described herein are transdermal delivery devices that deliver a local anesthetic to an injection or lancing site. The term "injection site" is the location on the subject's skin that is going to be punctured by a medical device including but not limited to a needle or lancet. The delivery device includes at least one resealable injection port and at least one local anesthetic reservoir. Each component of the delivery device is described in detail below and in the figures. The term injection port includes a resealable injection port which may be injected with a needle or pierced by a lancet.

The resealable injection port is generally composed of a polymeric, non-allergenic, non-reacting, inert material that permits a medical device such as a syringe or needle to readily pass through the material. During injection, the polymeric material forms a seal around the medical device. Upon removal of the medical device, the polymeric material substantially if not completely closes the hole produced by the medical device. Thus, the resealable injection port can maintain a sterile environment during injection and post-injection. The polymeric material used to make the resealable injection port can be composed of a variety of different materials such as, for example, silicon, non-allergic rubberized material, or other medically safe synthetic or semi-synthetic plastics. The number of injection ports can vary, as will be demonstrated below.

The delivery device also contains one or more local anesthetic reservoirs for holding the local anesthetic. The local anesthetic is generally positioned near the resealable injection port so that the skin at or near the injection site is exposed to the anesthetic and block the nerves of the skin, for a painless entry of a needle or lancet. The local anesthetic can be any topical anesthetic known in the art. In one aspect, the local anesthetic includes ester based or an amide based local anesthetics or any combination thereof. Examples of amide based local anesthetics include, but are not limited to, articaine, bupicaine, dibucaine, lidocaine, mepivacaine, prilocaine, and ropivacaine. Examples of ester based local anesthetics include, but are not limited to, benzocaine, chloroprocaine, proparacaine, and tetracaine. In one aspect, the local anesthetic is a combination of both lidocaine and prilocaine. The lidocaine and prilocaine are present at least in a 2:1 ratio by weight, a 1:1 ratio by weight, or any combination thereof. In other aspects, lidocaine and prilocaine may be present in the amount of 3:1, 4:1, 5:1, 6:1, 7:1, 8:1, 9:1, 10:1, 11:1, 12:1, 13:1, 14:1, 15:1. In addition, any of the local anesthetics mentioned above can be used in combination and are present at least in a 2:1, 3:1, 4:1, 5:1, 6:1, 7:1, 8:1, 9:1, 10:1, 11:1, 12:1, 13:1, 14:1, or 15:1 ratio by weight. Even up to 2:98, 5:95, 10:90, 25:75, 35:65, 50:50 amount respectively. The anesthetic can be mixed with carriers such as lipophilic vehicles in order to enhance the absorption of the anesthetic by the skin. The local anesthetic may be fast-acting or short-acting. For example, one may feel a "numbing" sensation within a matter of minutes. However, this numbing sensation may only last a matter of minutes or hours. In another aspect, the local anesthetic may be long acting. In this aspect, one may feel a "numbing" sensation rather quickly (i.e. in a matter of minutes), and this sensation may last up to at least 18 hours. The selection and amount of the local anesthetic can vary depending upon the size of the delivery device as well as the number and position of resealable injection ports present in the device and how long the patch will be used. The shape and size of the transdermal delivery device can vary depending upon the application, which is demonstrated in the figures. In certain aspects, the shape of the device is a circle, a square, a rectangle, an oval, an oblong shape, a triangle, a star, or a square depending upon where on the subject the device is applied. In general, the device has an adhesive that permits the attachment of the device to the skin of the subject. For example, the transdermal delivery device may be placed onto a finger (like a band aid), the abdomen, thigh, calf, arm, shoulder, or any other regions of exposed skin on the subject. Adhesives typically used in bandages and the like can be used herein.

The devices described herein can contain one or more optional therapeutic agents. The location of the optional therapeutic agents in the device can vary depending upon the design of the device. In one aspect, the optional therapeutic agent can be an antiseptic agent, a therapeutic pharmacological, a biologic, a nutriceutical, hormones, antibiotics, nicotine, antifungal agents, antiviral agents, or any pain relieving agent not excluding narcotics. By preventing bacterial, viral, and fungal growth, antiseptic agents maintain sterility either before, during, or post injection. In one aspect, the antiseptic agent can be an alcohol including, but not limited to, ethanol, propanol, isopropanol, or any combination thereof; quaternary ammonium compounds including, but not limited to, benzalkonium chloride, cetyl trimethylammonium bromide, cetylpyridinium chloride, benzethonium chloride, or any combination thereof; boric acid; chlorhexidine gluconate, hydrogen peroxide, iodine, mercurochrome, ocetnidine dihydrochloride, sodium chloride, sodium hypochlorite, colloidal silver, silver nitrate, mupirocin, erthromycin, clindamycin, gentamicin, polymyxin, bacitracin, silver, sulfadiazine, or any combination thereof.

In other aspects, the optional therapeutic agent is a vasoconstrictor. Vasoconstriction is the narrowing of blood vessels resulting from the contraction of the muscular wall of the vessels. When blood vessels constrict, the flow of blood is restricted or slowed. Without wishing to be bound by theory, a vasoconstrictor would increase the time a local anesthetic resided at one location. The vasoconstrictor may prevent blood flow washout or dissipation of the local anesthetic. In addition, a vasoconstrictor may limit the amount of bleeding associated with a needle or lancet stick. Such vasoconstrictors may include phenylephrine, ephedrine sulfate, epinephrine, naphazoline, neosynephrine, vasoxyl, oxymetazoline, or any combination thereof.

In another aspect, the optional therapeutic agent is a skin permeability enhancer. The skin is a rigid, almost impermeable layer. This impermeability is attributed to the nature of one very thin top surface layer called the stratum corneum. This impermeability creates problems for the transdermal delivery of agents which include local anesthetics. Examples of skin permeability enhancers include but are not limited to dimethyl sulfoxide (DMSO), lecithin, decyl methyl sulfoxide, dodecyl dimethyl phosphine oxide, octyl methyl sulfoxide, nonyl methyl sulfoxide, undecyl methyl sulfoxide, lauryl alcohol, diisopropyl sebacate, oleyl alcohol, diethyl sebacate, dioctyl sebacate, dioctyl azelate, hexyl laurate, ethyl caprate, butyl stearate, dibutyl sebacate, dioctyl adipate, propylene glycol dipelargonate, ethyl laurate, butyl laurate, ethyl myristate, butyl myristate, isopropyl palmitate, isopropyl isostearate, 2-ethylhexyl pelargonate, butyl benzoate, benzyl benzoate, benzyl salicylate, dibutyl phthalate, nicotinates, fatty acids, fatty alcohols, or any combination thereof. In one aspect, the skin permeability enhancer is at least greater than 1% weight per volume, weight per weight, or mole percent. In another aspect, the skin permeability enhancer may be at least greater than 1.5%, 2.0%, 2.5%, 3.0%, 3.5%, 4.0%, 4.5% up to 50% weight per volume, weight per weight, or mole percent. In one aspect, the skin permeability enhancer is dimethyl sulfoxide. In this aspect, the amount of dimethyl sulfoxide may range from 2% to 10%, 2% to 9.5%, 3% to 8%, 3% to 7%, or 4% to 6% weight per volume, weight per weight, by mole percent or any effective therapeutic amount relative to the local anesthetic.

In other aspects, anti-inflammatories and anti-dolorosa can be present in the device to reduce inflammation. This class of drugs functions to block various inflammatory pathways. For example, non-steroidal anti-inflammatory drugs (NSAIDs) alleviate pain and inflammation by counteracting cyclooxygenase and preventing the synthesis of prostaglandins. In one aspect, NSAIDs may be incorporated in the replaceable button or the semi-permeable reservoir of the transdermal delivery device. These NSAIDs may include celecoxib, meloxicam, nabumetone, piroxicam, naproxen, oxaprozin, rofecoxib, sulindac, ketoprofen, valdecoxid, anti-tumor necrosis factors, anti-cytokines, anti-inflammatory pain causing bradykinins or any combination thereof.

In another aspect, antihistamines and steroids can be used to prevent any allergic reaction or irritation caused by the anesthetic or other therapeutic agents when the device is used for prolonged periods of time.

In another aspect, transdermal transport of a local anesthetic and a therapeutic agent can be enhanced by the application of a secondary driving force either before or after application of the transdermal delivery device. In certain aspects this secondary driving force includes electromotive (electrotransport) force in the form of iontophoresis, electroosmosis, electroporation, fractional laser; or mechanical force such as magnetic force, vibration, vibroacoustic force, or sonophoretic force such as ultrasound. This force may be applied to enhance the uptake of the local anesthetic into subcutaneous tissue for rapid blocking of pain conduction nerve endings. For example, without wishing to be bound by theory, when ultrasound is used, low frequency is used. In one aspect, less than 2.5 MHz is used. In yet another aspect, less than 1 MHz is used. When acoustical vibrations (low frequency ultrasound with vibration—Vibroacoustic) are applied using a specified pulse ranging, from one-half second to three seconds, modulated with an oscillatory signal in the frequency range of 1 Hz to 1500 Hz, and having pulse amplitude in the range of about 20 to 5000 microns, transdermal transport of a local anesthetic and a therapeutic agent may be further enhanced.

Figure 1:
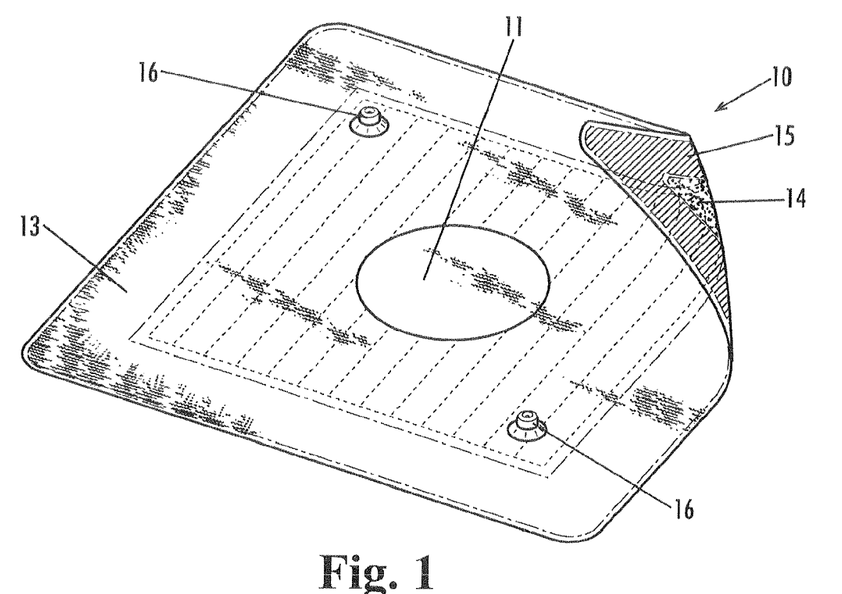
FIG. 1 shows the top view of a transdermal delivery device with a single injection port, two resealable refill ports, and an anesthetic reservoir.
Figure 2:
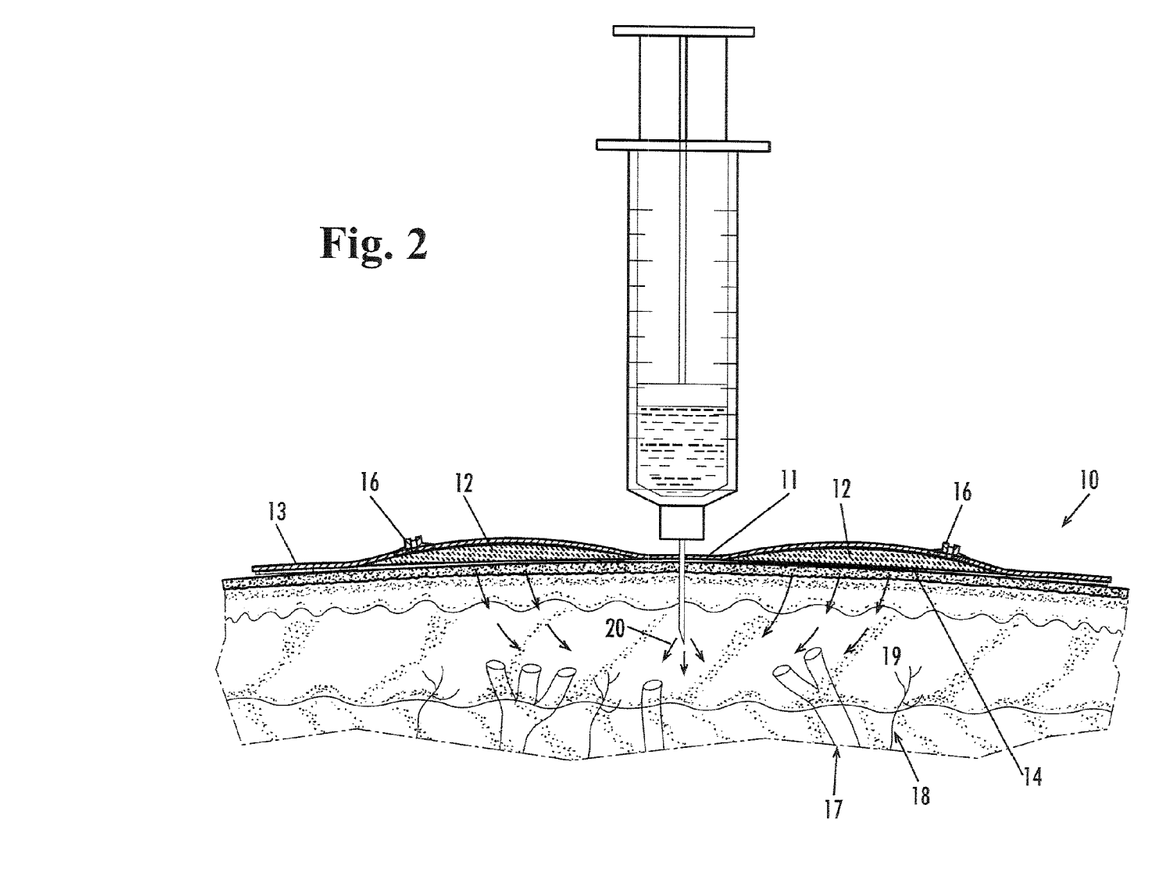
FIG. 2 shows the cross-sectional view of a transdermal delivery device with a single injection port, two resealable refill ports, and an anesthetic reservoir.

FIGS. 1-6 provide numerous designs of the devices described herein. Referring to FIGS. 1 and 2, the transdermal delivery device 10 is a patch having a resealable injection port 11 and a reservoir 12 that contains the local anesthetic or any other pharmaceutically acceptable preparation. On the topside of the device 10, an impermeable substrate 13 surrounds the injection port 11 and prevents the local anesthetic from leaching out of the reservoir. On the underside of the device 10, which is the side that is applied to the surface of the skin, an opposing permeable layer 14 is present and positioned under the reservoir 12. The permeable layer permits the diffusion of the local anesthetic from the reservoir to the skin surface. The permeable layer 14 is surrounded by an impermeable material 15, which prevents the local anesthetic from leaching to the sides of the device 10. An adhesive can be applied to the impermeable material 15, which helps adhere the device to the subject's skin. Semipermeable and permeable membranes may include, but are not limited to, materials made from regenerated cellulose, regenerated cellophane, cellulose ester membranes, charge mosaic membranes, bipolar membranes, amphoteric exchange membranes, anion exchange membranes, dialysis tubing, ethylene-vinyl acetate (EVA) copolymer membranes (e.g. 1-20% vinyl acetate), polyvinylalcohol (PVA) gels, or silicon films.

The device as shown in FIGS. 1 and 2 also permits refilling of the reservoir 12 with local anesthetic or other therapeutic pharmacological agents, biologics, and nutriceuticals once the anesthetic has substantially or completely diffused from the reservoir. Two resealable refill ports 16 are present in the device 10. The number and design of the ports can vary. For example, with smaller devices, the refill port can be composed of a polymeric material such as that used in the injection port, which permits the injection of additional anesthetic into the reservoir without a refill port. The selection of the polymeric material will depend upon the volume of the reservoir in the device and if present, the dimensions of the refill port. If larger devices are contemplated, the refill port can be accessed by a screw top. Thus, the delivery devices depicted in FIGS. 1-3 can be refilled and reused multiple times.

FIG. 2 further depicts inserting a hypodermic needle into the injection port and injecting a bioactive agent 20 within the dermal or subdermal layers. Within this figure, the contents of the reservoir (i.e. local anesthetic, vasoconstrictor, anti-histamine, etc.) are diffusing 19 into the epidermis, dermis, and subdermal layers of the skin. The diffused contents of the reservoir act on the nerves 18 and blood vessels 17 around the transdermal delivery device.

Figure 3:
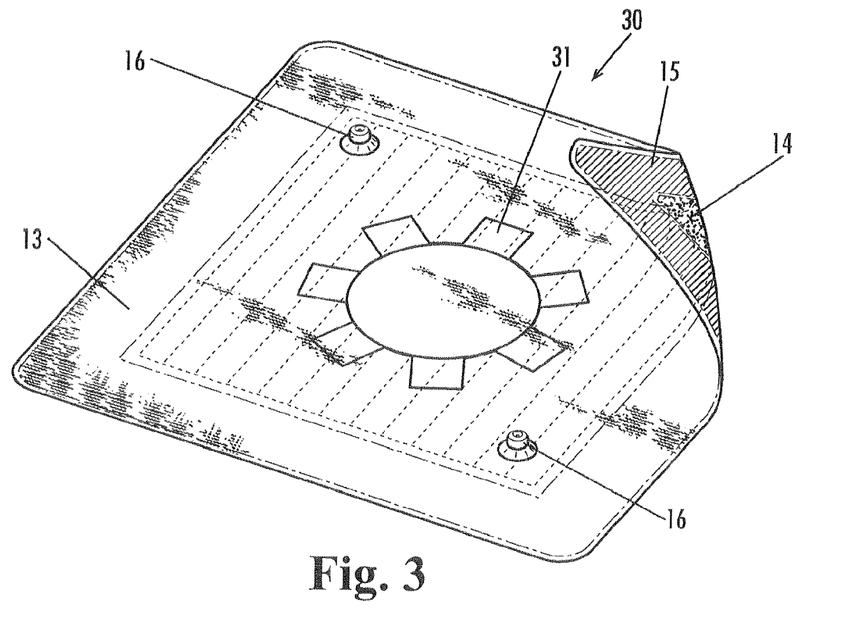
FIG. 3 shows the top view of a transdermal delivery device with multiple injection ports, two resealable refill ports, and an anesthetic reservoir.

FIG. 3 depicts a variation of the device 10 in FIG. 1. Referring to FIG. 3, device 30 has a seven injection ports 31. This device can be used for injection seven consecutive times. These injections may occur within one day or over a period of several days. Although not shown, an optional tether may be placed on the underside of the patch. This tether is a thin string made of metal, synthetic plastic, or semi-synthetic plastic which may connect the injection ports to one another. This tether functions to support each injection port and to prevent any resealable injection port from being dislodged or dislocated while removing a device such as a needle or lancet from the resealable injection port.

Figure 4:
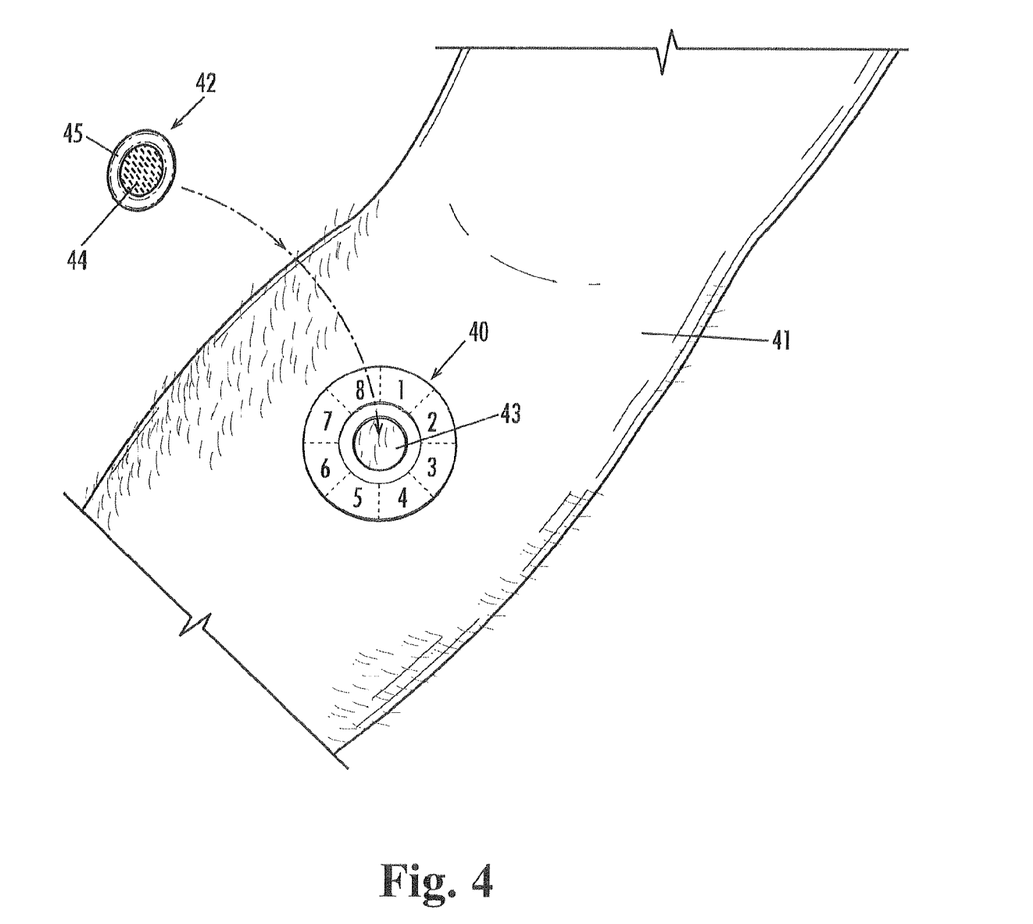
FIG. 4 shows a transdermal delivery device with a replaceable button with and an injection port having multiple adjacent resealable injection regions.

FIG. 4 provides another example of a delivery device having multiple injection ports in a circle so that the injection sites are rotated. Referring to FIG. 4, the device is composed of resealable injection port 40, which is shown as attached to the skin 41 of the subject, and a replaceable anesthetic button 42. The resealable injection port 40 as shown in FIG. 4 has eight injection regions, which means that the device can be used eight times before discarding the injection port 40. The injection port 40 can have an adhesive on the backside so that it can be affixed to the skin of the subject for extended periods of time. The resealable injection port 40 has an opening 43 for receiving the replaceable anesthetic button 42. The top and sides of the button are composed of an impermeable material, while the underside of the button that is in contact with the skin is composed of a permeable material. The impermeable and permeable materials described above can be used to produce the button 42. An adhesive is present on the surface 45 of the button, which helps adhere the button to the skin prior to injection. The volume of anesthetic present in the button will vary on the dimension of the button. In general, when the subject is ready to perform an injection, the replaceable anesthetic button is inserted into the injection port 40 for a sufficient time to numb the desired region of skin. An injection may be administered to injection region number one. When the next injection is administered, injection region number two will be used, and this will occur until all eight injection regions are used. The number of injection regions is not limited in number. After the injection, the replaceable anesthetic button is removed for future use. The injection port 40 can remain on the skin of the subject until all of the injection regions have been used.

Figure 5:
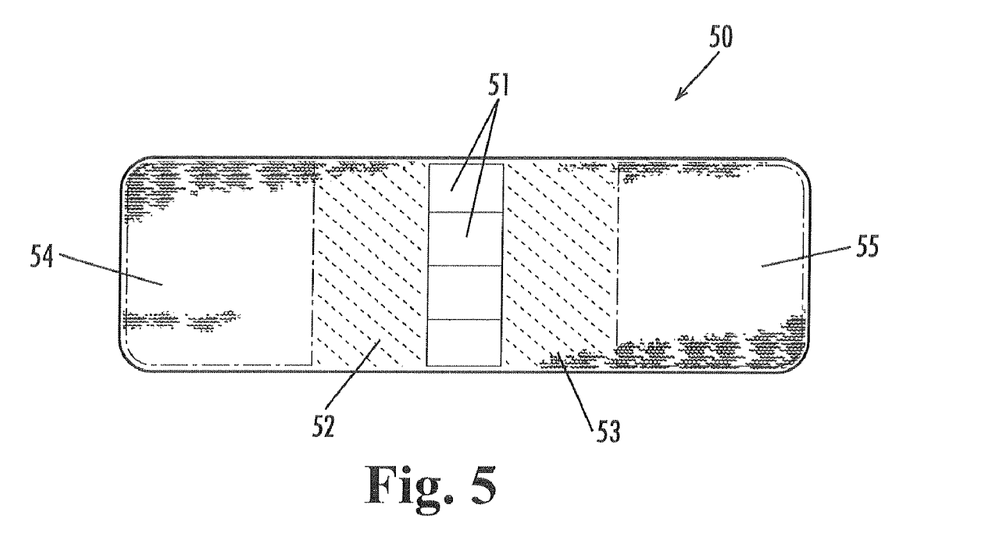
FIG. 5 shows a transdermal delivery device with multiple resealable injection ports surrounded by two anesthetic reservoirs without local anesthetic refill ports.
Figure 6:
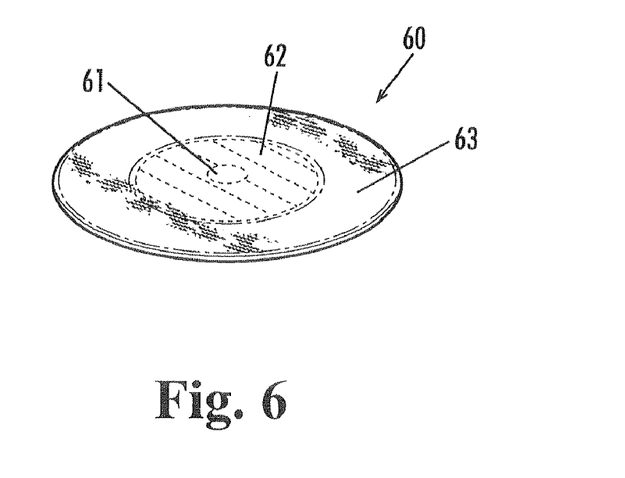
FIG. 6 shows a transdermal delivery device with a single resealable injection port surrounded by an anesthetic reservoir without a local anesthetic refill port.

FIGS. 5 and 6 depict additional devices described herein. As drawn, neither device has a resealable refill port for the local anesthetic; however, these features can easily be added by one of ordinary skill in the art, if desired. FIG. 5 shows the underside of device 50 (i.e., the side that is applied to the skin). The device 50 is composed of four resealable injection ports 51. In this aspect, anesthetic reservoirs 52 and 53 are adjacent to the injection ports. An adhesive can be applied to the surfaces 54 and 55, which are composed of an impermeable material. Although not shown in FIG. 5, a protective cover can be applied to the underside of the device 50 (and any of the other devices described herein) to prevent the anesthetic from leaking as well as decontamination of the injection port. The protective cover can be readily peeled off of the device 50 prior to use.

FIG. 6 shows another design of the delivery device. The underside of device 60 as shown in FIG. 6 has a resealable injection port 61 surrounded by an anesthetic reservoir 62, where the anesthetic can diffuse from the reservoir to the surface of the skin through a permeable or semipermeable membrane. An adhesive is applied to the surface 63. The surface 63 and the backside of device 60 are composed of an impermeable material.

The optional therapeutic agents described above can be incorporated in a number of different locations within the delivery device. For example, an antiseptic agent can be applied to the surface of the injection port (topside and/or underside) to kill any bacteria, virus, or fungus that may be present on the syringe and maintain a sterile environment at the injection site. Alternatively, in order to maintain a sterile environment at the injection port, the injection port can be covered with an antiseptic cap or cover. In other aspects, one or more therapeutic agents can be mixed with the anesthetic and the mixture introduced into the anesthetic reservoir. In this aspect, the therapeutic agent diffuses to the skin with the anesthetic.

The devices described herein can be applied to the skin of a subject where the skin is ultimately going to be punctured in order to reduce or eliminate pain associated with the puncture. The underside of the injection port(s) has non irritating adhesive which will facilitate sticking to the skin when applied. Such adhesive may include a topical silicone adhesive, a water based adhesive, epoxies, urethanes, methacrylates, polyacrylates, rubber-based adhesives, polysiloxane adhesives, pressure sensitives, starches, and phenolics of varying tack levels depending on the patient's skin and the task at hand. The adhesive material may be an acrylic adhesive including at least one polymer selected from homopolymers of acrylic esters, copolymers of two or more types of acrylic ester units and copolymers of acrylic esters and other functional monomers. Acyrlic esters include, but are not limited to, butyl(meth)acrylate, pentyl(meth)acrylate, hexyl(meth)acrylate, heptyl(meth)acrylate, octy(meth)acrylate, nonyl(meth)acrylate, decyl(meth)acrylate. Functional monomers include, but are not limited to, monomers containing a hydroxyl group, such as hydroxyethyl(meth)acrylate, hydroxypropyl(meth)acrylate, monomers containing a carboxyl group such as carboxyl methacrylate and monomers containing an amide group such as methacrylamide, dimethylmethacrylamide, etc.

Specific examples of acrylate monomers, which are suitable for use with the present invention include, but are not limited to methacrylic acid, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, dodecylmethacrylate, tridecyl acrylate, tridecyl methacrylate, and mixtures thereof.

Specific examples of functional monomers which are copolymerizable with the above-recited alkyl acrylates or methacrylates, which can also be used include, but are not limited to acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, and mixtures thereof.

Specific examples of suitable rubber-based pressure sensitive adhesives include but are not limited to hydrocarbon polymers, such as natural and synthetic polyisoprenes, polybutylenes, polyisobutylene (PIB), styrene/butadiene polymers, styrene-isoprene-styrene block copolymers, hydrocarbon polymers such as butyl rubber, halogen-containing polymers such as polyacrylic nitrile, polytetrafluoroethylene, polyvinyl chloride, polyvinylidene chloride, and polychlorodiene, and polysiloxane, and other copolymers thereof.

Specific examples of polysiloxanes include but not limited to silicone pressure sensitive adhesives, which are based on two major components: a polymer, or gum, and a tackifying resin. The polysiloxane adhesive may be prepared by cross-linking the gum, typically a high molecular weight polydiorganosiloxane with the resin to produce a three-dimensional silicate structure via a condensation reaction in an appropriate organic solvent. Various aspects of formulating polysiloxane adhesives are known in the art. Suitable silicone pressure-sensitive adhesives are commercially available and include the silicone adhesives sold as BIO-PSA®, Dow Corning Corporation, Medical Products, Midland, Mich.

As described above, the local anesthetic diffuses from the anesthetic reservoir onto the skin. The local anesthetic numbs a portion of the skin at or near the injection site. The duration of contact between the skin and the anesthetic can vary depending upon the type of puncture or injection that is made. In one aspect, the device is applied 30 to 60 minutes in advance to allow the local anesthetic to enter the dermal never fibers in the skin and block them so that when the injection occurs, the subject does not feel pain. The devices described herein have numerous applications including, but not limited to, reducing or eliminating pain associated with the injection of bioactive agents such as drugs and both pediatric and adult vaccines; the drawing of blood from a subject; the use of permanent infusion ports; the use of artery-venous (A-V) shunts used in kidney dialysis; the use of ports to inject various steroids and other therapeutic agents into the diseased or damaged tissue such as muscles, tendons, and joints; their use by podiatrists for corns; their use as a band aid to draw the blood droplets to test for glucose levels in diabetics and other blood chemistry analysis; and the insertion of canulas for intravenous infusion, catheters, PICC lines for long IV infusions, Swan Ganz catheter intersection, nerve blocks to relive pain, and injections of painful joints.

The devices described herein are particularly useful in the treatment of chronic disorders, systemic diseases, and hormone replacement therapy. Such chronic and systemic diseases include, for example, diabetes, psoriasis, and eczema. In the case of diabetes, the subject is continuously monitoring blood sugar levels as well as self-administering insulin. The continuous pricking and injections can be traumatic to the subject over time. The devices described herein alleviate the pain and stress associated with this, which will ultimately ensure that the subject is diligent with monitoring their blood sugar levels and consistently administering their medication.

In another aspect, the transdermal delivery device can be used for reducing or eliminating pain associated with bruises, cuts, poison ivy irritation, insect bites and stings, localized skin diseases, and allergic reactions without using the injection port.

In yet another aspect, the transdermal delivery device can be used to deliver either locally or systemically any one of the substances, chemicals, hormones, or therapeutic agents mentioned above.

Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A transdermal delivery device comprising at least one re-sealable injection port and at least one local anesthetic reservoir for delivering the anesthetic to the skin of a subject, wherein the at least one local anesthetic reservoir surrounds the at least one re-sealable injection port, and the re-sealable injection port is separated from the local anesthetic reservoir by an impermeable substrate.

2. The transdermal delivery device of claim 1, wherein the device further comprises at least one re-sealable refill port for refilling the local anesthetic reservoir.

3. The transdermal delivery separated from the local anesthetic reservoir of claim 1, wherein the device comprises a first side and second side, wherein the first side comprises an impermeable material surrounding the injection port, the second side comprises a permeable or semi-permeable material, wherein the impermeable material of the first side and the permeable or semi-permeable material of the second side forms the local anesthetic reservoir, and the permeable or semi-permeable material permits the diffusion of the local anesthetic from the local anesthetic reservoir.

4. The transdermal delivery device of claim 3, wherein the periphery of the permeable or semi-permeable material on the second side is surrounded by a second impermeable material.

5. The transdermal delivery device of claim 4, wherein an adhesive is present on the surface of the second impermeable material.

6. The transdermal delivery device of claim 3, wherein one or more re-sealable refill ports are present on the first side of the device.

7. The transdermal delivery device of claim 3, wherein the device comprises two or more injection ports.

8. The transdermal delivery device of claim 1, wherein the local anesthetic comprises an ester based local anesthetic, an amide based local anesthetic, or a combination thereof.

9. The transdermal delivery device of claim 8, wherein the amide based local anesthetic comprises articaine, bupivacaine, dibucaine, lidocaine, mepivacaine, prilocaine, ropivacaine, or any combination thereof.

10. The transdermal delivery device of claim 8, wherein the amide based local anesthetic comprises lidocaine, prilocaine, or a combination thereof.

11. The transdermal delivery device of claim 10, wherein when lidocaine and prilocaine are present, they are present in at least a ratio of 2:1 by weight.

12. The transdermal delivery device of claim 8, wherein the ester based local anesthetic comprises benzocaine, chloroprocaine, proparacaine, tetracaine, or any combination thereof.

13. The transdermal delivery device of claim 1, wherein an antiseptic agent is coated on at least one surface of the at least one re-sealable injection port.

14. The transdermal delivery device of claim 1, wherein an antiseptic agent is coated on both surfaces of the at least one re-sealable injection port.

15. The transdermal delivery device of claim 13, wherein the antiseptic agent, comprises an alcohol, a quaternary ammonium compounds comprising benzalkonium chloride, cetyl trimethylammonium bromide, boric acid, chlorhexidine gluconate, hydrogen peroxide, iodine, mercurochrome, octenidine dihydrochloride, sodium chloride, sodium hypochlorite, silver nitrate, or any combination thereof.

16. The transdermal delivery device of claim 1, wherein the device further comprises one or more therapeutic agents admixed with the local anesthetic.

17. The transdermal delivery device of claim 16, wherein the therapeutic agent comprises a vasoconstrictor, a skin permeability enhancer, an anti-inflammatory agent, an antihistamine, or any combination thereof.

18. The transdermal delivery device of claim 17, wherein the vasoconstrictor comprises phenylephrine, ephedrine sulfate, epinephrine, naphazoline, neosynephrine, vasoxyl, oxymetazoline, or any combination thereof.

19. The transdermal delivery device of claim 17, wherein the skin permeability enhancer comprises dimethyl sulfoxide, lecithin, decyl methyl sulfoxide, dodecyl dimethyl phosphine oxide, octyl methyl sulfoxide, nonyl methyl sulfoxide, undecyl methyl sulfoxide, lauryl alcohol, diisopropyl sebacate, oleyl alcohol, diethyl sebacate, dioctyl sebacate, dioctyl azelate, hexyl laurate, ethyl caprate, butyl stearate, dibutyl sebacate, dioctyl adipate, propylene glycol dipelargonate, ethyl laurate, butyl laurate, ethyl myristate, butyl myristate, isopropyl palmitate, isopropyl isostearate, 2-ethylhexyl pelargonate, butyl benzoate, benzyl benzoate, benzyl salicylate, dibutyl phthalate, or any combination thereof.

20. The transdermal delivery device of claim 17, wherein the anti-inflammatory agent comprises celecoxib, meloxicam, nabumetone, piroxicam, naproxen, oxaprozin, rofecoxib, sulindac, ketoprofen, valdecoxib, or any combination thereof.

21. The transdermal delivery device of claim 1, further comprising a short acting anesthetic, a long acting anesthetic, or any combination thereof having a predetermined volume.

22. A method for reducing or eliminating pain associated with a syringe, needle stick, or lancet stick comprising (a) applying the transdermal delivery device of claim 1 on the surface of the skin of a subject for a sufficient time to numb the skin, and (b) inserting the syringe, needle stick, or lancet stick in the resealable injection port.

23. A method for reducing or eliminating pain comprising applying the transdermal delivery device of claim 1 to the skin wherein the skin is bruised, cut, irritated by poison ivy or insect stings and bites or localized skin diseases, or affected by allergic reactions without using the injection port.

* * * * *